US012403592B1

(12) United States Patent
Berme et al.

(10) Patent No.: US 12,403,592 B1
(45) Date of Patent: Sep. 2, 2025

(54) MOTION BASE FOR DISPLACING AN OBJECT ABOVE A SUPPORT SURFACE

(71) Applicant: Bertec Corporation, Columbus, OH (US)

(72) Inventors: Necip Berme, Worthington, OH (US); Sasan Ghassab, Worthington, OH (US); Toby L. Baumgartner, Canal Winchester, OH (US); Geoffrey Lee Brown, Columbus, OH (US); Anthony Ethan Oddo, Seattle, WA (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 18/789,531

(22) Filed: Jul. 30, 2024

Related U.S. Application Data

(60) Provisional application No. 63/529,742, filed on Jul. 30, 2023.

(51) Int. Cl.
| | |
|---|---|
| *B25J 9/16* | (2006.01) |
| *A61B 5/103* | (2006.01) |
| *A63B 22/00* | (2006.01) |
| *A63B 24/00* | (2006.01) |
| *A63B 26/00* | (2006.01) |
| *G01M 1/12* | (2006.01) |
| *G09B 9/14* | (2006.01) |

(52) U.S. Cl.
CPC .......... *B25J 9/1623* (2013.01); *A61B 5/1036* (2013.01); *A63B 26/003* (2013.01); *G01M 1/122* (2013.01); *G09B 9/14* (2013.01)

(58) Field of Classification Search
CPC ............ A63B 26/003; A63B 2026/006; A61B 5/1036; B25J 9/1623
See application file for complete search history.

(56) References Cited

U.S. PATENT DOCUMENTS

| | | | | |
|---|---|---|---|---|
| 5,941,807 | A | * | 8/1999 | Cassidy ............. A63B 21/4009 482/130 |
| 6,038,488 | A | | 3/2000 | Barnes et al. |
| 6,113,237 | A | | 9/2000 | Ober et al. |
| 6,152,564 | A | | 11/2000 | Ober et al. |
| 6,295,878 | B1 | | 10/2001 | Berme |
| 6,354,155 | B1 | | 3/2002 | Berme |
| 6,389,883 | B1 | | 5/2002 | Berme et al. |

(Continued)

FOREIGN PATENT DOCUMENTS

| | | | | | |
|---|---|---|---|---|---|
| CN | 116035866 | A | * | 5/2023 | ........... A61H 1/0237 |
| DE | 102012016604 | A1 | * | 6/2014 | ............... A61B 5/11 |

(Continued)

*Primary Examiner* — Joshua T Kennedy
(74) *Attorney, Agent, or Firm* — The Law Office of Patrick F. O'Reilly III, LLC

(57) ABSTRACT

A motion base for displacing an object above a support surface includes a base support structure; a displaceable carriage configured to be coupled to an object; and an actuation system, the actuation system including one or more actuators operatively coupling the displaceable carriage to the base support structure, the one or more actuators configured to displace the displaceable carriage relative to the base support structure. In one or more embodiments, a portion of the displaceable carriage is suspended below a portion of the one or more actuators of the actuation system.

20 Claims, 13 Drawing Sheets

(56) References Cited

U.S. PATENT DOCUMENTS

| | | | |
|---|---|---|---|
| 6,936,016 B2 | 8/2005 | Berme et al. | |
| 6,942,487 B2 * | 9/2005 | Corbalis | A63B 69/0093 |
| | | | 472/91 |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 9,916,011 B1 | 3/2018 | Berme et al. | |
| 9,927,312 B1 * | 3/2018 | Berme | A63B 22/025 |
| 10,010,248 B1 | 7/2018 | Shearer | |
| 10,010,286 B1 | 7/2018 | Berme et al. | |
| 10,085,676 B1 | 10/2018 | Berme et al. | |
| 10,117,602 B1 | 11/2018 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,264,964 B1 | 4/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,463,250 B1 | 11/2019 | Berme et al. | |
| 10,527,508 B2 | 1/2020 | Berme et al. | |
| 10,555,688 B1 | 2/2020 | Berme et al. | |
| 10,646,153 B1 | 5/2020 | Berme et al. | |
| 10,722,114 B1 | 7/2020 | Berme et al. | |
| 10,736,545 B1 | 8/2020 | Berme et al. | |
| 10,765,936 B2 | 9/2020 | Berme et al. | |
| 10,803,990 B1 | 10/2020 | Wilson et al. | |
| 10,853,970 B1 | 12/2020 | Akbas et al. | |
| 10,856,796 B1 | 12/2020 | Berme et al. | |
| 10,860,843 B1 | 12/2020 | Berme et al. | |
| 10,945,599 B1 | 3/2021 | Berme et al. | |
| 10,966,606 B1 | 4/2021 | Berme | |
| 11,033,453 B1 | 6/2021 | Berme et al. | |
| 11,052,288 B1 | 7/2021 | Berme et al. | |
| 11,054,325 B2 | 7/2021 | Berme et al. | |
| 11,074,711 B1 | 7/2021 | Akbas et al. | |
| 11,097,154 B1 | 8/2021 | Berme et al. | |
| 11,158,422 B1 | 10/2021 | Wilson et al. | |
| 11,182,924 B1 | 11/2021 | Akbas et al. | |
| 11,262,231 B1 | 3/2022 | Berme et al. | |
| 11,262,258 B2 | 3/2022 | Berme et al. | |
| 11,301,045 B1 | 4/2022 | Berme et al. | |
| 11,311,209 B1 | 4/2022 | Berme et al. | |
| 11,321,868 B1 | 5/2022 | Akbas et al. | |
| 11,337,606 B1 | 5/2022 | Berme et al. | |
| 11,348,279 B1 | 5/2022 | Akbas et al. | |
| 11,458,362 B1 | 10/2022 | Berme et al. | |
| 11,521,373 B1 | 12/2022 | Akbas et al. | |
| 11,540,744 B1 | 1/2023 | Berme | |
| 11,604,106 B2 | 3/2023 | Berme et al. | |
| 11,631,193 B1 | 4/2023 | Akbas et al. | |
| 11,688,139 B1 | 6/2023 | Karagoz et al. | |
| 11,705,244 B1 | 7/2023 | Berme | |
| 11,712,162 B1 | 8/2023 | Berme et al. | |
| 11,790,536 B1 | 10/2023 | Berme et al. | |
| 11,798,182 B1 | 10/2023 | Karagoz et al. | |
| 11,816,258 B1 | 11/2023 | Berme et al. | |
| 11,826,601 B1 | 11/2023 | Berme | |
| 11,850,078 B1 | 12/2023 | Berme | |
| 11,857,331 B1 | 1/2024 | Berme et al. | |
| 11,865,407 B1 | 1/2024 | Berme et al. | |
| 11,911,147 B1 | 2/2024 | Berme et al. | |
| 11,992,746 B1 | 5/2024 | Berme | |
| 12,013,542 B1 | 6/2024 | Berme et al. | |
| 12,094,159 B1 | 9/2024 | Akbas et al. | |
| 2003/0199374 A1 * | 10/2003 | Perry | A63B 22/18 |
| | | | 482/146 |
| 2003/0216656 A1 | 11/2003 | Berme et al. | |
| 2007/0027009 A1 * | 2/2007 | Arnold | A63B 21/005 |
| | | | 482/146 |
| 2008/0228110 A1 | 9/2008 | Berme | |
| 2011/0039669 A1 * | 2/2011 | Stewart | A63B 69/0053 |
| | | | 482/146 |
| 2011/0277562 A1 | 11/2011 | Berme | |
| 2012/0266648 A1 | 10/2012 | Berme et al. | |
| 2012/0271565 A1 | 10/2012 | Berme et al. | |
| 2014/0287895 A1 * | 9/2014 | Kern | A63B 21/0442 |
| | | | 482/147 |
| 2015/0096387 A1 | 4/2015 | Berme et al. | |
| 2015/0328497 A1 * | 11/2015 | Doucot | A63B 69/0057 |
| | | | 482/146 |
| 2016/0245711 A1 | 8/2016 | Berme et al. | |
| 2016/0334288 A1 | 11/2016 | Berme et al. | |
| 2018/0024015 A1 | 1/2018 | Berme et al. | |
| 2019/0078951 A1 | 3/2019 | Berme et al. | |
| 2020/0139229 A1 | 5/2020 | Berme et al. | |
| 2020/0289896 A1 * | 9/2020 | Kikuchi | A63B 22/20 |
| 2020/0408625 A1 | 12/2020 | Berme et al. | |
| 2021/0197027 A1 * | 7/2021 | D'Alesio | A63B 22/18 |
| 2021/0333163 A1 | 10/2021 | Berme et al. | |
| 2022/0178775 A1 | 6/2022 | Berme et al. | |

FOREIGN PATENT DOCUMENTS

| | | | | |
|---|---|---|---|---|
| DE | 102013220978 A1 * | 4/2015 | | A63B 21/4047 |
| DE | 202023001280 U1 * | 10/2023 | | A63B 22/14 |
| FR | 2963246 A1 * | 2/2012 | | A61H 1/0237 |

\* cited by examiner

SECTION A-A

MOTION BASE FOR DISPLACING AN OBJECT ABOVE A SUPPORT SURFACE

CROSS-REFERENCE TO RELATED APPLICATIONS

This patent application claims priority to, and incorporates by reference in its entirety, U.S. Provisional Patent Application No. 63/529,742, entitled "Motion Base For Displacing An Object Above A Support Surface", filed on Jul. 30, 2023.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a motion base for displacing an object mounted thereon. More particularly, the invention relates to a motion base for displacing a force measurement assembly, such as an instrumented treadmill or force plate.

2. Background

Motion bases are used to selectively displace an object mounted thereon. As one example, a force measurement assembly may be mounted on a motion base in order to selectively displace a subject disposed on the force measurement assembly. Conventional motion bases comprise a top plate or frame supported on a plurality of actuators. The object displaced by the motion base is mounted to the top plate or frame. The plurality of actuators selectively displaces the top plate or frame of the motion base, and the object mounted thereon, based upon input control signals sent to the actuators.

However, these conventional motion bases have numerous limitations and drawbacks. For example, some of these conventional motion bases have large footprints and provide limited degrees-of-freedom. As another example, when these conventional motion bases have rotational axes above the surface of the object being rotated, the structure of these motion bases can become undesirably complex.

What is needed, therefore, is a motion base with a compact footprint and multiple degrees-of-freedom. In addition, a motion base is needed with a rotational axis disposed beneath a top surface of an object being rotated so as to simplify the structural configuration of the motion base.

BRIEF SUMMARY OF EMBODIMENTS OF THE INVENTION

Accordingly, the present invention is directed to a motion base for displacing an object above a support surface that substantially obviates one or more problems resulting from the limitations and deficiencies of the related art.

In accordance with one or more embodiments of the present invention, there is provided a motion base for displacing an object above a support surface. The motion base includes a base support structure; a displaceable carriage configured to be coupled to the object; and an actuation system, the actuation system including one or more actuators operatively coupling the displaceable carriage to the base support structure, the one or more actuators configured to displace the displaceable carriage relative to the base support structure. In these one or more embodiments, a portion of the displaceable carriage is suspended below a portion of the one or more actuators of the actuation system.

In a further embodiment of the present invention, the base support structure at least partially surrounds the displaceable carriage.

In yet a further embodiment, the displaceable carriage comprises a top frame section, a bottom frame section, and at least one vertical frame member connected between the bottom frame section and the top frame section.

In still a further embodiment, the base support structure comprises at least one frame member disposed beneath a bottom surface of the displaceable carriage, and at least one of the one or more actuators of the actuation system is coupled between the at least one frame member of the base support structure and the top frame section of the displaceable carriage.

In yet a further embodiment, the displaceable carriage has a basket-like shape with an open rear side, and the object that is coupled to the displaceable carriage comprises a force measurement assembly for collecting force and/or moment data used in computerized dynamic posturography (CDP) testing and/or training performed on a person.

In still a further embodiment, the one or more actuators of the actuation system comprise a plurality of actuators, each of the plurality of actuators being coupled between a respective frame member of the base support structure and the top frame section of the displaceable carriage.

In yet a further embodiment, a rotatable upper end of at least one of the plurality of actuators is coupled to the top frame section of the displaceable carriage by a mounting plate.

In still a further embodiment, the motion base has at least two degrees of freedom.

In yet a further embodiment, the motion base has six degrees of freedom.

In still a further embodiment, the object that is coupled to the displaceable carriage comprises a force measurement assembly, and the force measurement assembly comprises a top surface for receiving at least one portion of a body of a person; and at least one force transducer, the at least one force transducer configured to sense one or more measured quantities and output one or more signals that are representative of forces and/or moments being applied to the top surface of the force measurement assembly by the person.

In yet a further embodiment, the motion base further comprises one or more data processing devices operatively coupled to the actuation system of the motion base and the force measurement assembly, the one or more data processing devices configured to receive the one or more signals that are representative of the forces and/or moments being applied to the top surface of the force measurement assembly by the person, and to convert the one or more signals into output forces and/or moments, the one or more data processing devices further configured to selectively displace the force measurement assembly using the actuation system of the motion base.

In accordance with one or more other embodiments of the present invention, there is provided a motion base for displacing an object above a support surface. The motion base includes a base assembly; a support structure configured to be coupled to the object, the support structure being rotatably coupled to the base assembly about a transverse rotational axis, the transverse rotational axis being disposed beneath a top surface of the object; and an actuation system, the actuation system including one or more actuators operatively coupled to the support structure, and the one or more actuators configured to rotate the support structure relative to the base assembly about the transverse rotational axis and translate the support structure so as to simulate a rotation of the support structure about an imaginary rotational axis disposed above the top surface of the object.

In a further embodiment of the present invention, the one or more actuators are configured to simultaneously translate the support structure while rotating the support structure about the transverse rotational axis so as to simulate the rotation of the support structure about the imaginary rotational axis disposed above the top surface of the object.

In yet a further embodiment, the object that is coupled to the support structure comprises one of: (i) an instrumented treadmill, (ii) a force plate, (iii) a flight simulator, and (iv) a virtual reality simulator.

In still a further embodiment, the one or more actuators comprise a first actuator configured to rotate the support structure about the transverse rotational axis and a second actuator configured to translate the support structure.

In accordance with yet one or more other embodiments of the present invention, there is provided a motion base for displacing a force measurement assembly. The motion base includes a base assembly; a support structure configured to be coupled to the force measurement assembly, the support structure being rotatably coupled to the base assembly about a transverse rotational axis, the transverse rotational axis being disposed beneath a top surface of the force measurement assembly; and an actuation system, the actuation system including one or more actuators operatively coupled to the support structure, and the one or more actuators configured to rotate the support structure relative to the base assembly about the transverse rotational axis and translate the support structure so as to simulate a rotation of the support structure about an imaginary rotational axis disposed above the top surface of the force measurement assembly.

In a further embodiment of the present invention, wherein the one or more actuators are configured to simultaneously translate the support structure while rotating the support structure about the transverse rotational axis so as to simulate the rotation of the support structure about the imaginary rotational axis disposed above the top surface of the force measurement assembly.

In yet a further embodiment, the force measurement assembly comprises one of: (i) an instrumented treadmill and (ii) a force plate.

In still a further embodiment, the force measurement assembly is configured to acquire force and/or moment data used in computerized dynamic posturography (CDP) testing and/or training performed on a person.

In yet a further embodiment, the one or more actuators comprise a first actuator configured to rotate the support structure about the transverse rotational axis and a second actuator configured to translate the support structure.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
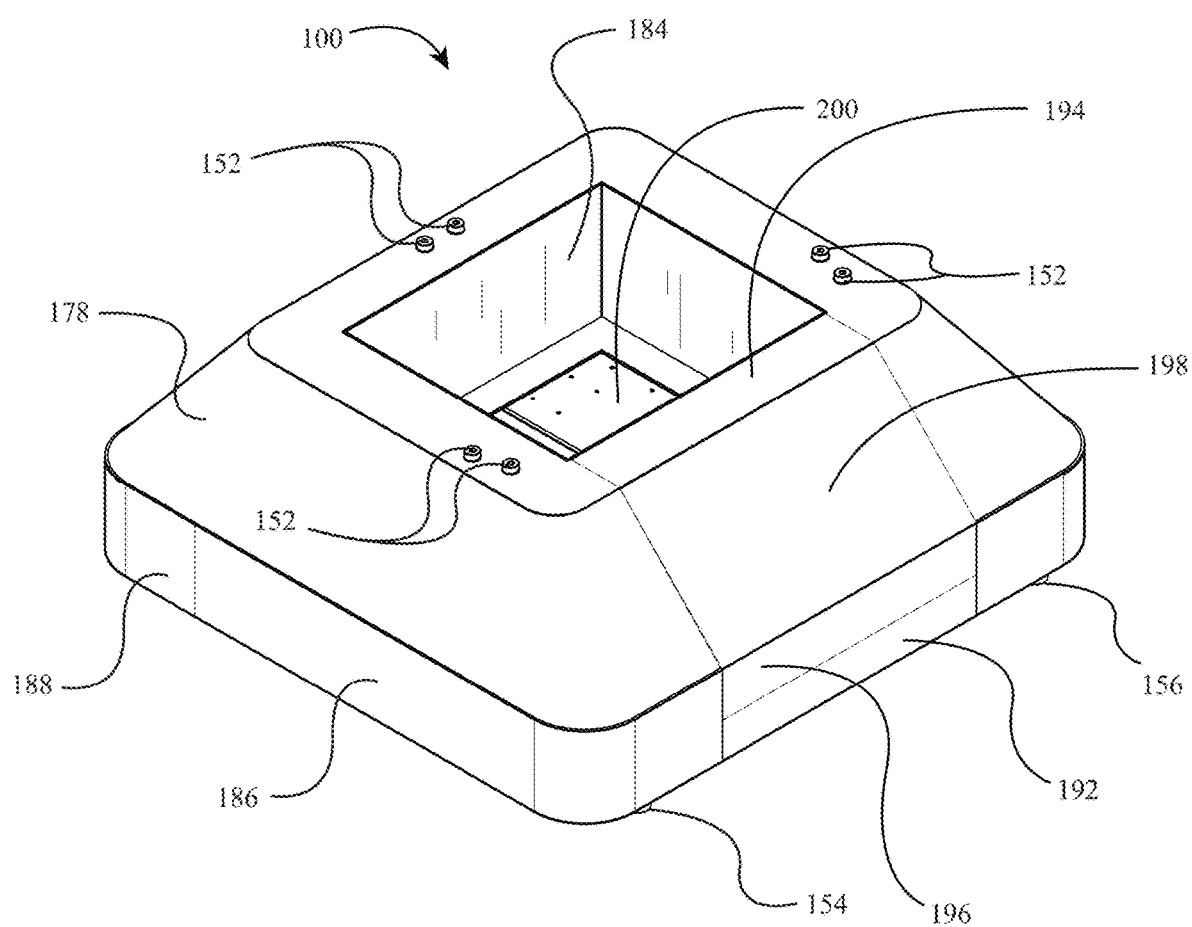
FIG. 1 is a perspective view of a motion base in accordance with a first illustrative embodiment, wherein a force plate is mounted on the motion base and the motion base is provided with cover members thereon.
Figure 2:
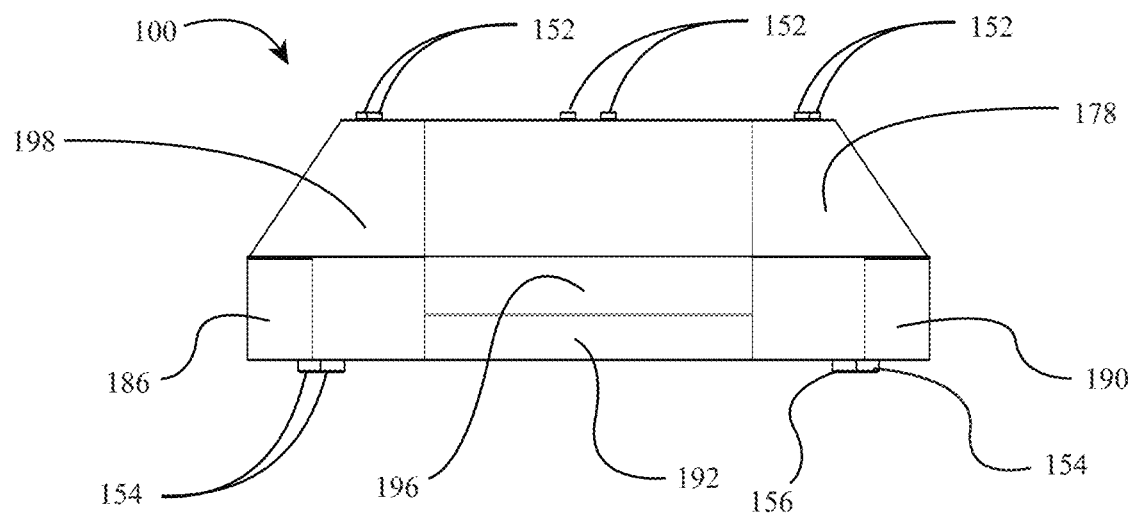
FIG. 2 is a rear elevational view of the motion base of FIG. 1.
Figure 3:
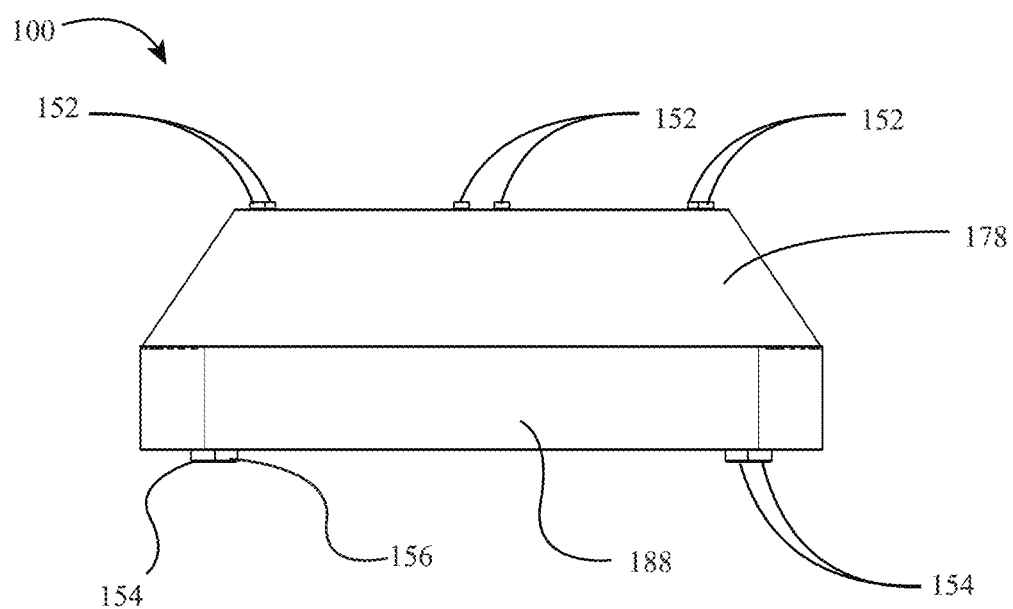
FIG. 3 is a front elevational view of the motion base of FIG. 1.
Figure 4:
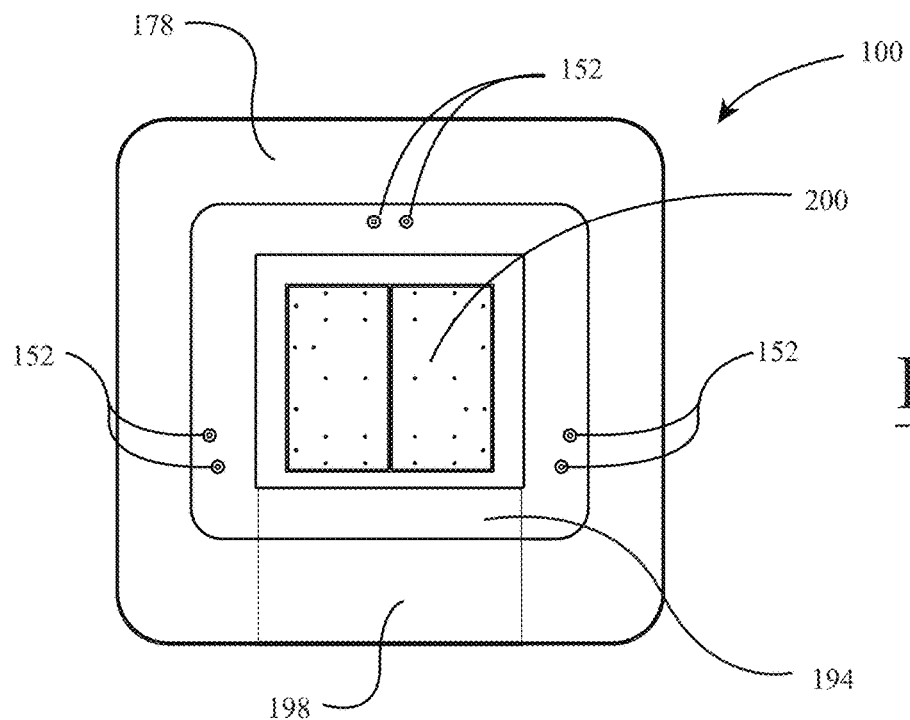
FIG. 4 is a top plan view of the motion base of FIG. 1.
Figure 5:
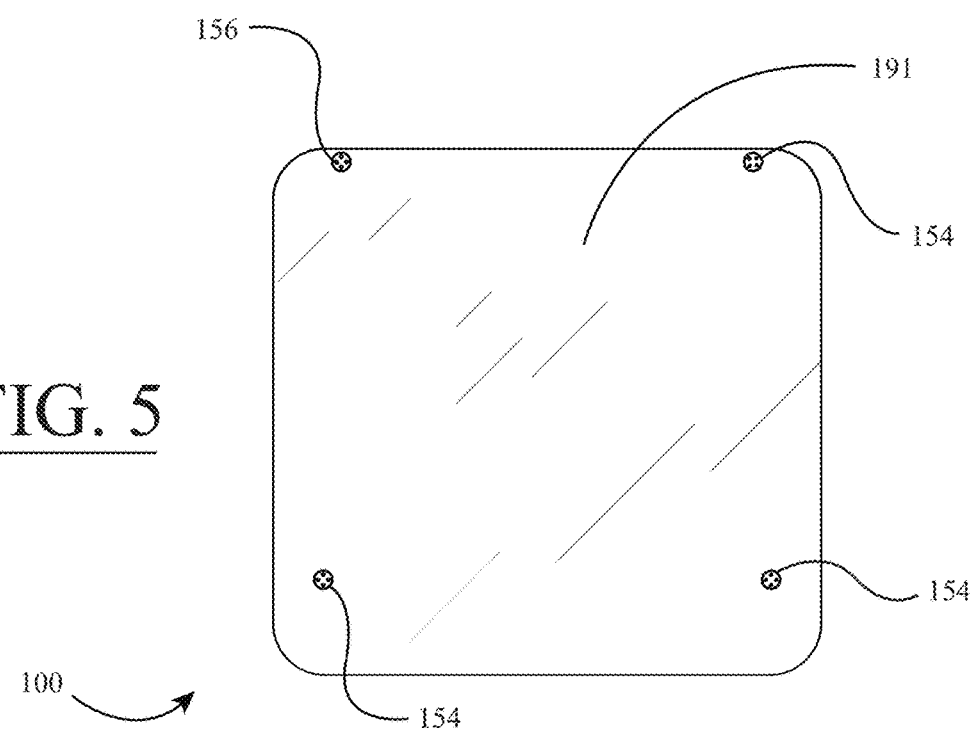
FIG. 5 is a bottom plan view of the motion base of FIG. 1.
Figure 15:
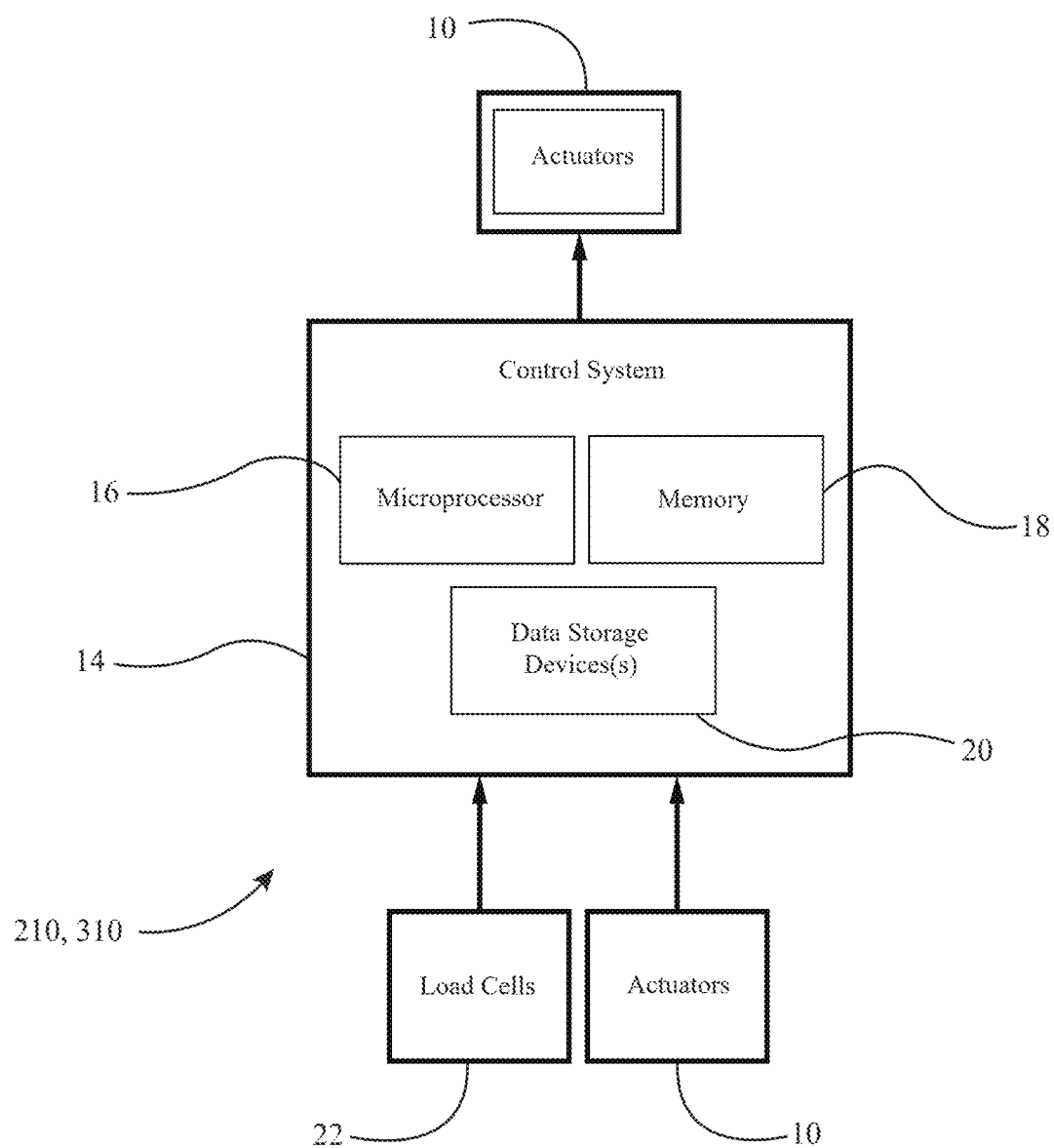
FIG. 15 is a block diagram of constituent components of force measurement systems comprising the motion bases described herein.
Figure 16:
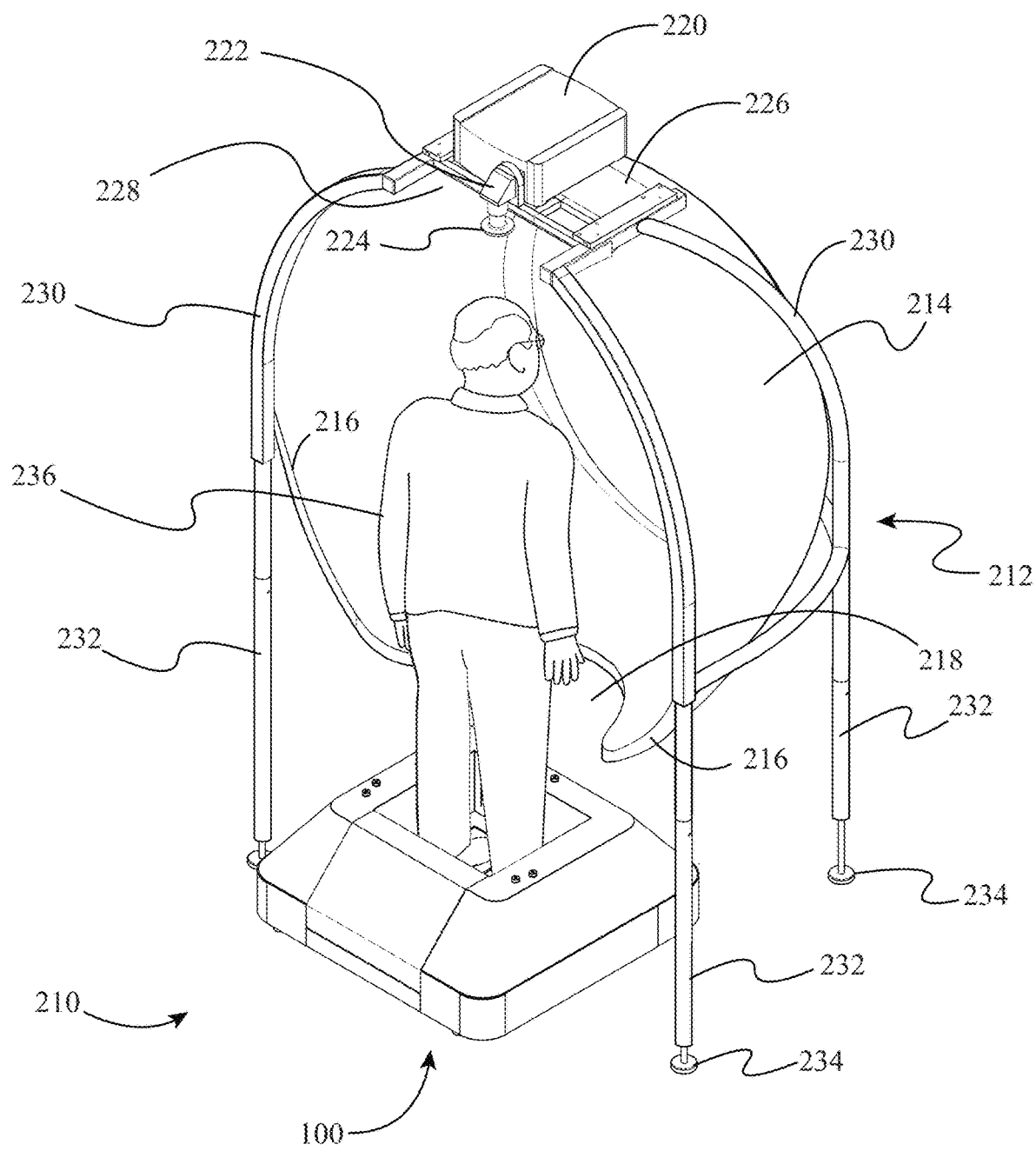
FIG. 16 is a perspective view of a force measurement system comprising the motion base of FIG. 1 and an immersive subject visual display device, according to the first illustrative embodiment.
Figure 17:
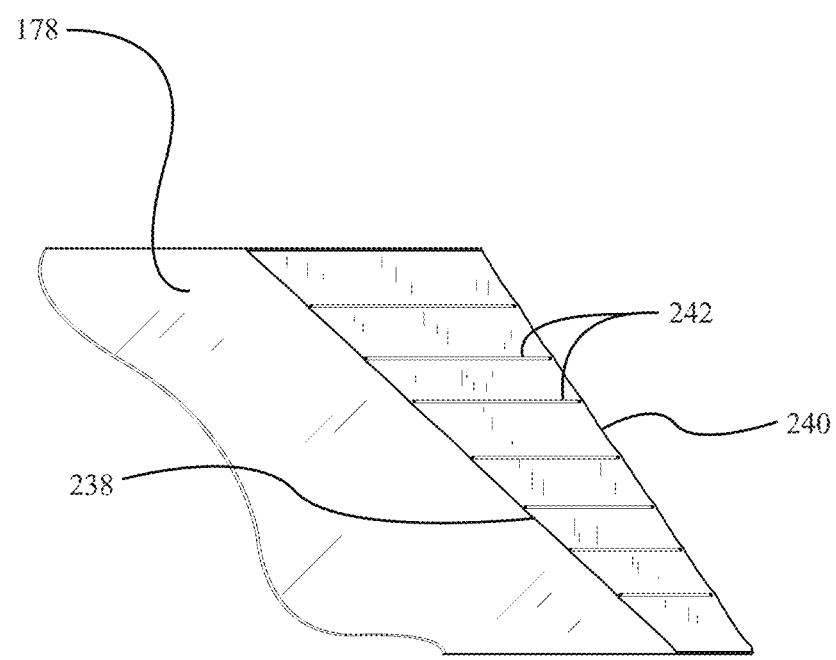
FIG. 17 is a sectional view cut through a flexible bellows member of the motion base of FIG. 1, wherein the section is generally cut along the cutting-plane line A-A in FIG. 7.

In a first illustrative embodiment, with reference initially to FIGS. 1, 15, and 16, a force measurement system 210 may comprise a force measurement assembly (e.g., a force plate 200) mounted on a displaceable carriage of a motion base 100, an immersive visual display device 212, and one or more data processing devices 14 operatively coupled to the force plate 200, the actuation system of the motion base 100, and the immersive visual display device 212. In this illustrative embodiment, the one or more data processing devices 14 are configured to receive the one or more signals that are representative of the forces and/or moments being applied to the top surface of the force plate 200 by the subject, and to convert the one or more signals into output forces and/or moments. The one or more data processing devices 14 are further configured to selectively displace the force plate 200 using the actuation system of the motion base 100. The motion base 100 will be described in detail hereinafter.

Figure 8:
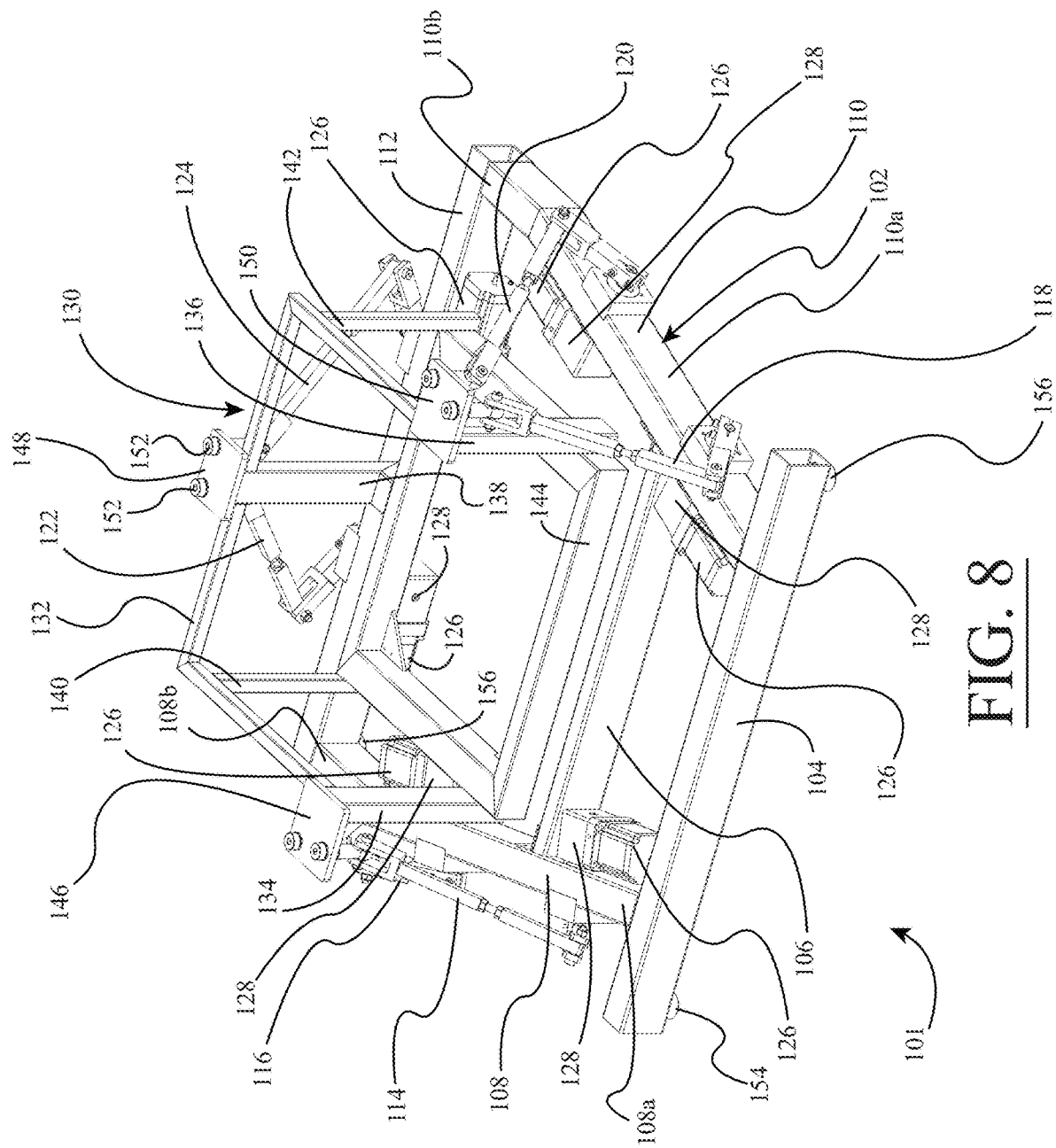
FIG. 8 is a perspective view of the internal assembly of the motion base of FIG. 1, wherein the cover members have been removed from the motion base.
Figure 9:
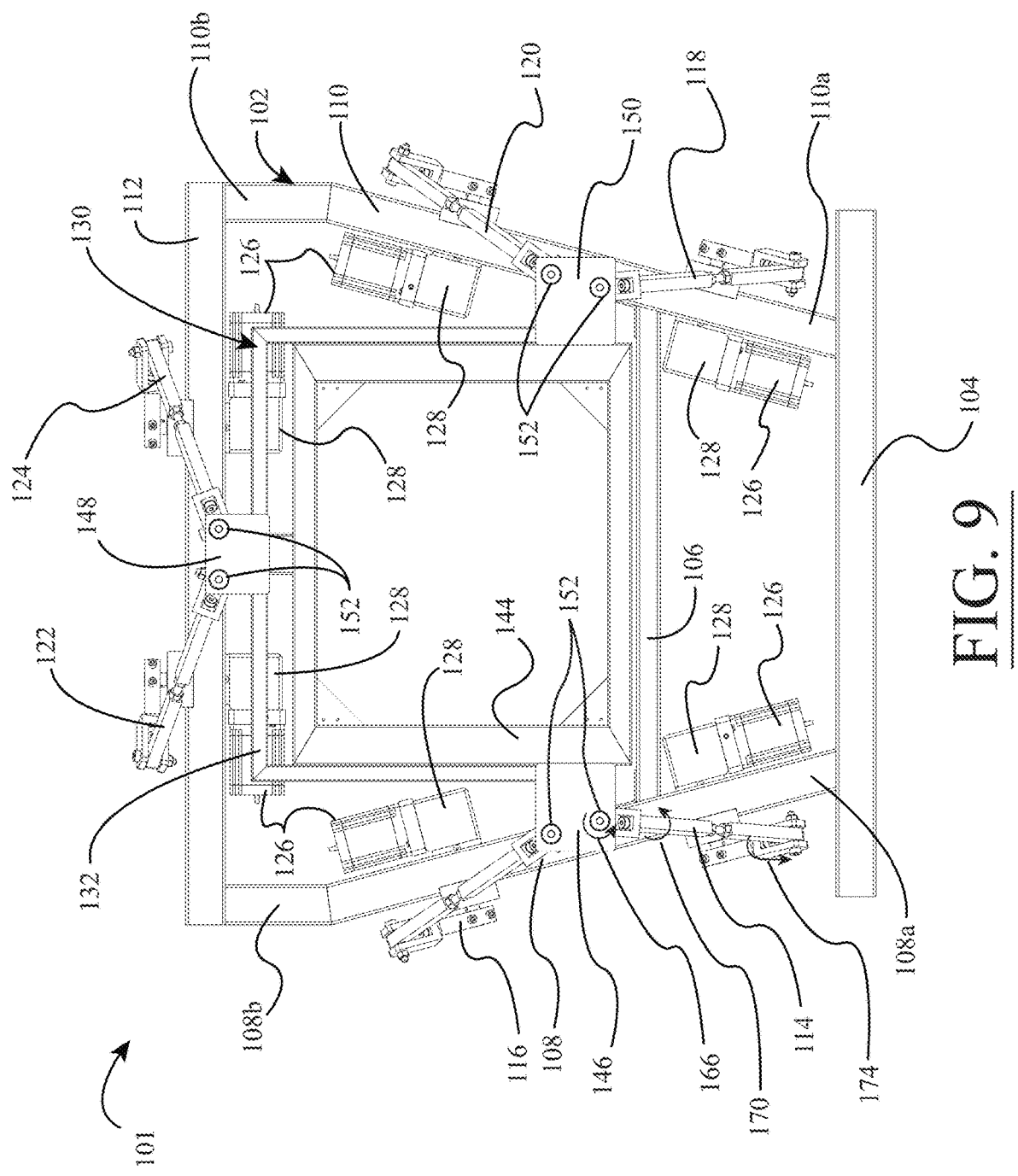
FIG. 9 is a top plan view of the internal assembly of the motion base of FIG. 8.
Figure 10:
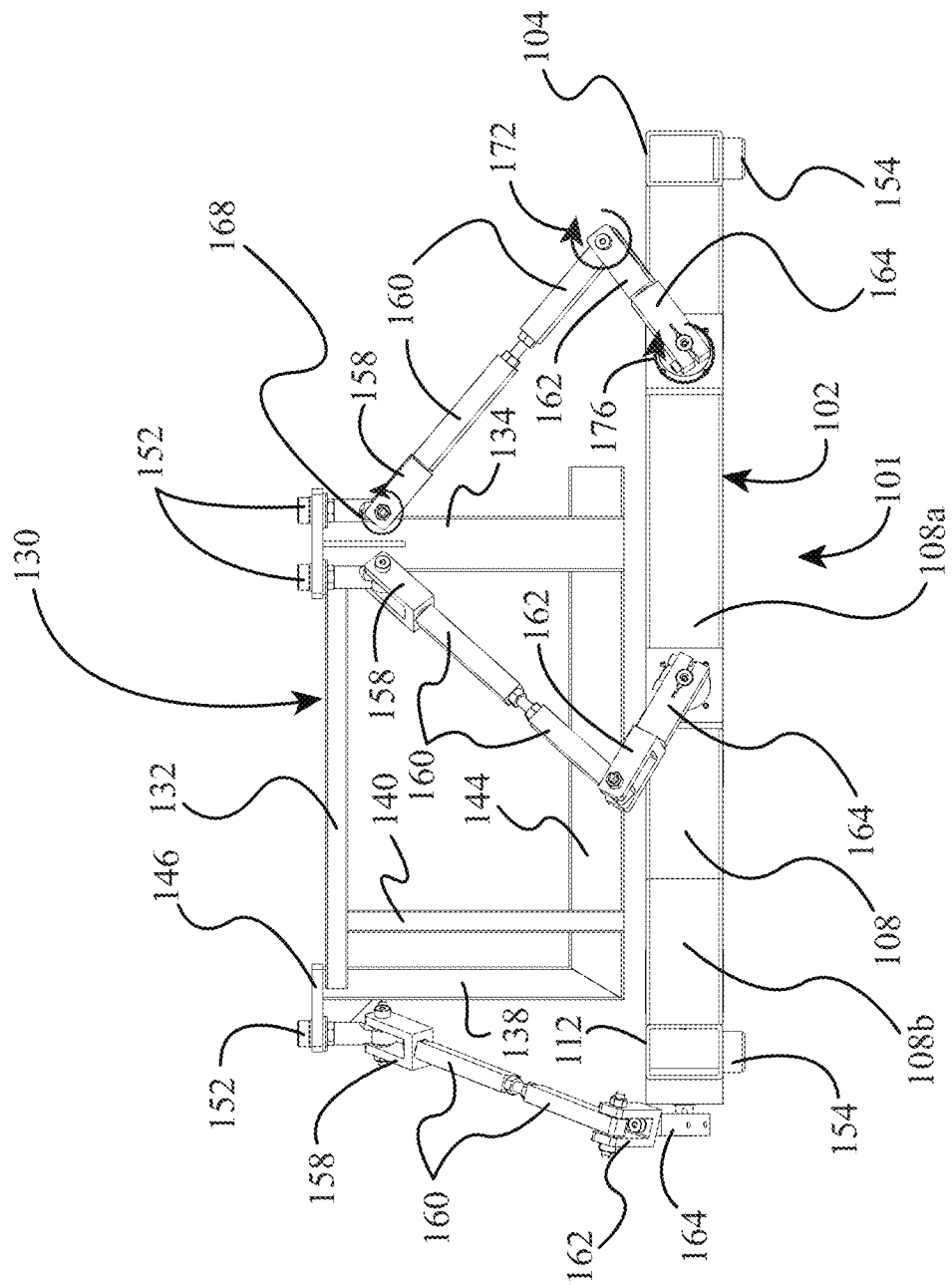
FIG. 10 is a side elevational view of the internal assembly of the motion base of FIG. 8.

Initially, referring to FIGS. 8-10, the internal assembly 101 of the motion base 100 will now be described in detail. As shown in FIG. 8, the internal assembly 101 of the motion base 100 generally comprises a base support structure 102; a displaceable carriage 130 configured to be coupled to an object (e.g., the force plate 200); and an actuation system including a plurality of actuators 114, 116, 118, 120, 122, 124 operatively coupling the displaceable carriage 130 to the base support structure 102. The plurality of actuators 114, 116, 118, 120, 122, 124 are configured to displace the displaceable carriage 130 relative to the support structure 102. As shown in FIGS. 8 and 10, a portion of the displaceable carriage 130 is suspended below a portion of the plurality of actuators 114, 116, 118, 120, 122, 124 of the actuation system (i.e., the displaceable carriage 130 is suspension-mounted from top end portions of the actuators 114, 116, 118, 120, 122, 124). As depicted in FIGS. 8 and 10, the displaceable carriage 130 of the motion base 100 is preferably displaceable (i.e., translatable) and rotatable in 3-dimensional space by means of the plurality of actuators 114, 116, 118, 120, 122, 124. In other words, the motion base 100 is preferably a six (6) degree-of-freedom motion base. In the illustrative embodiment, the motion base 100 is used for the dynamic testing of subjects when, for example, the subject is being tested, or is undergoing training, in a virtual reality environment. For example, the force plate 200 may be used for collecting force and/or moment data used in computerized dynamic posturography (CDP) testing and/or training performed on a person. Also, in the illustrative embodiment, the motion base 100 is able to accommodate any type of perturbations as inputs (i.e., any type of perturbations generated by the one or more data processing devices 14. While the displaceable carriage 130 of the motion base 100 is preferably translatable and rotatable in 3-dimensional space, it is to be understood that the motion base is not so limited. Rather, in alternative embodiments, the motion base 100 is provided with lesser degrees of motion.

In the illustrative embodiment, as shown in FIG. 8, the base support structure 102 comprises a first frame member 104, a second frame member 106, a third frame member 108, a fourth frame member 110, and a fifth frame member 112. Referring again to FIG. 8, it can be seen that the third frame member 108, which comprises a diagonal portion 108a and a straight portion 108b, is disposed on a first side of the motion base 100. The fourth frame member 110, which comprises a diagonal portion 110a and a straight portion 110b, is disposed on a second, opposite side of the motion base 100. The first frame member 104 is connected to rear ends of the diagonal portions 108a, 110a of the third and fourth frame members 108, 110, while the second frame member 106 is connected to interior sides of the diagonal portions 108a, 110a of the third and fourth frame members 108, 110. The fifth frame member 112 is connected to front ends of the straight portions 108b, 110b of the third and fourth frame members 108, 110. In the illustrative embodiment, the frame members 104, 106, 108, 110, 112 of the base support structure 102 may be welded to one another so as to form a base weldment. As shown in FIGS. 8 and 9, the base support structure 102 surrounds the displaceable carriage 130 and structurally supports the displaceable carriage 130. In the illustrative embodiment, referring to FIGS. 8 and 10, the frame members 104, 106, 108, 110, 112 of the base support structure 102 are disposed beneath a bottom surface of the displaceable carriage 130, and the plurality of actuators 114, 116, 118, 120, 122, 124 of the actuation system are coupled between frame members 108, 110, 112 of the base support structure 102 and a top frame section 132 of the displaceable carriage 130.

Referring again to FIG. 8, in the illustrative embodiment, it can be seen that the displaceable carriage 130 has a basket-like shape with an open rear side. With combined reference to FIGS. 8 and 10, the displaceable carriage 130 of the illustrative embodiment comprises the top C-shaped frame section 132, a first vertical support post 134, a second vertical support post 136, a third vertical support post 138, a fourth vertical support post 140, a fifth vertical support post 142, and a bottom rectangular frame section 144. The vertical support posts 134, 136, 138, 140, 142 connect the bottom rectangular frame section 144 to the top C-shaped frame section 132. In particular, referring again to FIGS. 8 and 10, the first and fourth vertical support posts 134, 140 connect the bottom rectangular frame section 144 to the top C-shaped frame section 132 on a first side of the displaceable carriage 130. The second and fifth vertical support posts 136, 142 connect the bottom rectangular frame section 144 to the top C-shaped frame section 132 on a second, opposite side of the displaceable carriage 130, and the third vertical support post 138 connects the bottom rectangular frame section 144 to the top C-shaped frame section 132 at the front of the displaceable carriage 130. In the illustrative embodiment, the frame members 132, 134, 136, 138, 140, 142, 144 of the displaceable carriage 130 may be welded to one another so as to form a carriage weldment.

In the illustrative embodiment, the displaceable carriage 130 is affixedly attached to the force plate 200 so that the force plate 200 is able to be displaced together with the displaceable carriage 130. In other alternative embodiments, other objects may be attached to the displaceable carriage 130 of the motion base 100, such as an instrumented treadmill or other objects for which the displacement thereof is desired. For example, when the displaceable carriage 130 is being used to displace an instrumented treadmill, the structure of the displaceable carriage 130 may be modified accordingly to accommodate the increased size of the instrumented treadmill.

Next, with reference again to FIGS. 8-10, the actuation system of the motion base 100 will be described in detail. As shown in these figures, in the illustrative embodiment, the actuation system of the motion base 100 generally comprises six (6) actuators 114, 116, 118, 120, 122, 124 configured to displace the displaceable carriage 130 and the force plate 200 supported thereon relative to the base support structure 102 of the motion base 100. In FIGS. 8 and 10, it can be seen that each of the actuators 114, 116, 118, 120, 122, 124 is connected between one of the frame members 108, 110, 112 of the base support structure 102 and the top frame section 132 of the displaceable carriage 130. More specifically, as shown in FIGS. 8 and 9, the top frame section 132 of the displaceable carriage 130 is provided with three (3) protruding mounting plates 146, 148, 150, wherein each of the mounting plates 146, 148, 150 accommodates one pair of the actuators 114, 116, 118, 120, 122, 124. The first and second actuators 114, 116 are connected between a sidewall of the diagonal portion 108a of the third frame member 108 of the base support structure 102 and the first mounting plate 146. The third and fourth actuators 118, 120 are connected between a sidewall of the diagonal portion 110a of the fourth frame member 110 of the base support structure 102 and the third mounting plate 150. The fifth and sixth actuators 122, 124 are connected between a sidewall of the fifth frame member 112 of the base support structure 102 and the second mounting plate 148. In the illustrative embodiment, as shown in FIGS. 8 and 9, each of the actuators 114, 116, 118, 120, 122, 124 is powered by an electric servo motor 126 that is operatively coupled to the arm members of the actuators 114, 116, 118, 120, 122, 124 by respective gearboxes 128.

Turning again to FIG. 10, in the illustrative embodiment, each actuator 114, 116, 118, 120, 122, 124 is connected to its respective mounting plate 146, 148, 150 by an actuator shoulder bolt 152. The actuator shoulder bolt 152 of each actuator 114, 116, 118, 120, 122, 124 is connected to a respective first clevis member 158 and, in turn, the first clevis member 158 is connected to an elongate arm member 160 of the actuator 114, 116, 118, 120, 122, 124. The elongate arm member 160 of each actuator 114, 116, 118, 120, 122, 124 is connected to a respective second clevis member 162 and, in turn, the second clevis member 162 is connected to a bottom connector member 164 of the actuator 114, 116, 118, 120, 122, 124. The bottom connector member 164 is affixed to a shaft of the gearbox 128 such that the bottom connector member 164 of each actuator 114, 116, 118, 120, 122, 124 is rotated by the respective actuator motor 126. In the illustrative embodiment, as shown in FIGS. 8-10, the elongate arm member 160 of each actuator 114, 116, 118, 120, 122, 124 may have a threaded fastener in the middle thereof that allows the length of the arm member 160 to be adjusted by a user for fine tuning the displacement of the displaceable carriage 130 (i.e., the adjustable length elongate arm members 160 allow the sides of the displaceable carriage 130 to be raised or lowered).

Turning again to FIGS. 9 and 10, the degrees-of-freedom (DOF) of the actuators 114, 116, 118, 120, 122, 124 will be described. In the illustrative embodiment, each actuator 114, 116, 118, 120, 122, 124 has a total of six (6) degrees-of-freedom (DOF). As an example, the six (6) degrees-of-freedom (DOF) will be described with regard to the first actuator 114, but it is to be understood that all of the other actuators 116, 118, 120, 122, 124 have the same degrees-of-freedom (DOF) as that described for the first actuator 114. Initially, as shown in FIG. 9, the first degree-of-freedom (DOF) rotation for the actuator 114 is about the rotational axis of the actuator shoulder bolt 152 (i.e., diagrammatically represented by the semi-circular arrow 166 in FIG. 9). Turning to FIG. 10, the second degree-of-freedom (DOF) rotation for the actuator 114 is about the rotational axis of the shoulder bolt passing through the first clevis member 158 (i.e., diagrammatically represented by the semi-circular arrow 168 in FIG. 10). Referring again to FIG. 9, the third degree-of-freedom (DOF) rotation for the actuator 114 is about the longitudinal rotational axis of the elongate arm member 160 (i.e., diagrammatically represented by the semi-circular arrow 170 in FIG. 9). Turning back to FIG. 10, the fourth degree-of-freedom (DOF) rotation for the actuator 114 is about the rotational axis of the shoulder bolt passing through the second clevis member 162 (i.e., diagrammatically represented by the semi-circular arrow 172 in FIG. 10). Referring again to FIG. 9, the fifth degree-of-freedom (DOF) rotation for the actuator 114 is about the longitudinal rotational axis of the second clevis member 162 (i.e., diagrammatically represented by the semi-circular arrow 174 in FIG. 9). Finally, referring again to FIG. 10, the sixth degree-of-freedom (DOF) rotation for the actuator 114 is about the rotational axis of the gearbox 128 (i.e., diagrammatically represented by the semi-circular arrow 176 in FIG. 10). In the illustrative embodiment, during displacement of the motion base 100, all of the actuator motors 126 are configured to be rotated at the same time.

In the illustrative embodiment, the motion base 100 utilizes six (6) pushrod driven actuators 114, 116, 118, 120, 122, 124 attached in pairs to three (3) positions on the base support structure 102, crossing over to three (3) mounting locations on the displaceable carriage 130. In the illustrative embodiment, all actuator connections are made via custom-machined joints to achieve precise position and motion control, while still allowing for the displaceable carriage 130 to lower completely to the base support structure 102 beneath.

Referring to FIGS. 1-3, 5, 8, and 10, in the illustrative embodiment, the motion base 100 is provided with a plurality of support feet 154, 156 disposed thereunder. Preferably, each of the four (4) corners of the motion base 100 is provided with a support foot 154 or 156. In the illustrative embodiment, each support foot 154, 156 is attached to a bottom surface of base support structure 102 (e.g., two (2) support feet 154, 156 may be attached to the first frame member 104 of the base support structure 102, and two (2) support feet 154 may be attached to the fifth frame member 112 of the base support structure 102). In the illustrative embodiment, at least one of the support feet 156 is adjustable so as to facilitate the leveling of the motion base 100 on an uneven floor surface (e.g., see FIG. 8, the adjustable support foot 156 can be provided with a threaded shaft that permits the height thereof to be adjusted).

Now, turning to FIGS. 1-7 and 17, the cover members of the illustrative motion base 100 will be described. Initially, with combined reference to FIGS. 1 and 7 of the illustrative embodiment, it can be seen that the motion base 100 comprises a top C-shaped cover member 180, a C-shaped bellows member 178, and an annular cover member 182 beneath the C-shaped flexible bellows member 178. Turning to the sectional view of FIG. 17, it can be seen that the C-shaped flexible bellows member 178 comprises an inner fabric layer 238, an outer fabric layer 240, and interior wire supports 242 disposed between the inner fabric layer 238 and the outer fabric layer 240. Advantageously, the flexible bellows member 178 allows the displaceable carriage 130 to be displaced relative to the base support structure 102.

Turning again to FIGS. 1 and 7, in the illustrative embodiment, it can be seen that the motion base 100 further comprises an internal C-shaped cover member 184 attached to the displaceable carriage 130. The base support structure 102 of the motion base 100 is provided with a first L-shaped side cover member 186, a front cover member 188, a second L-shaped side cover member 190, a bottom cover member 191, a rear cover member 192, and a floor cover member 196 (see FIG. 7). Advantageously, the cover members of the motion base 100 protect users of the motion base 100 from the internal components of the motion base 100, and give the motion base 100 a finished appearance.

Figure 6:
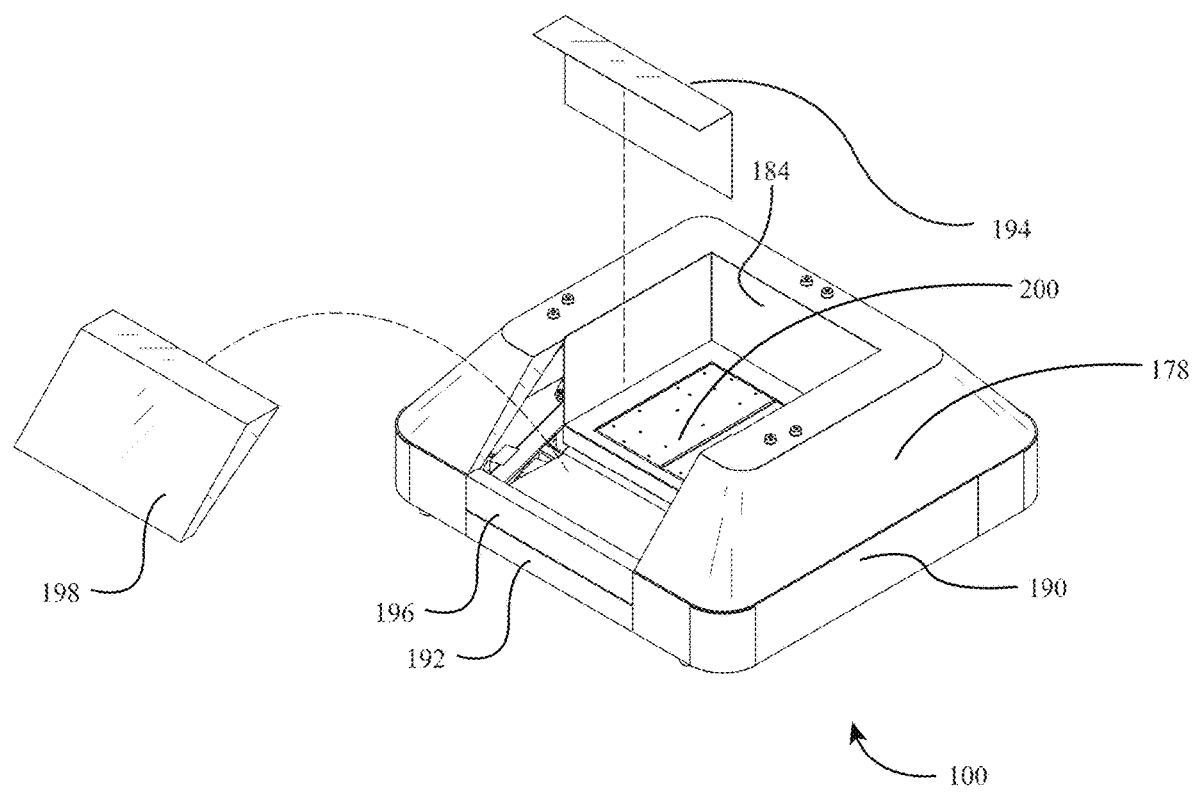
FIG. 6 is another perspective view of the motion base of FIG. 1, wherein removable cover members have been removed from the remainder of the motion base so as to allow a person to gain access to the force plate in the middle of the motion base.
Figure 7:
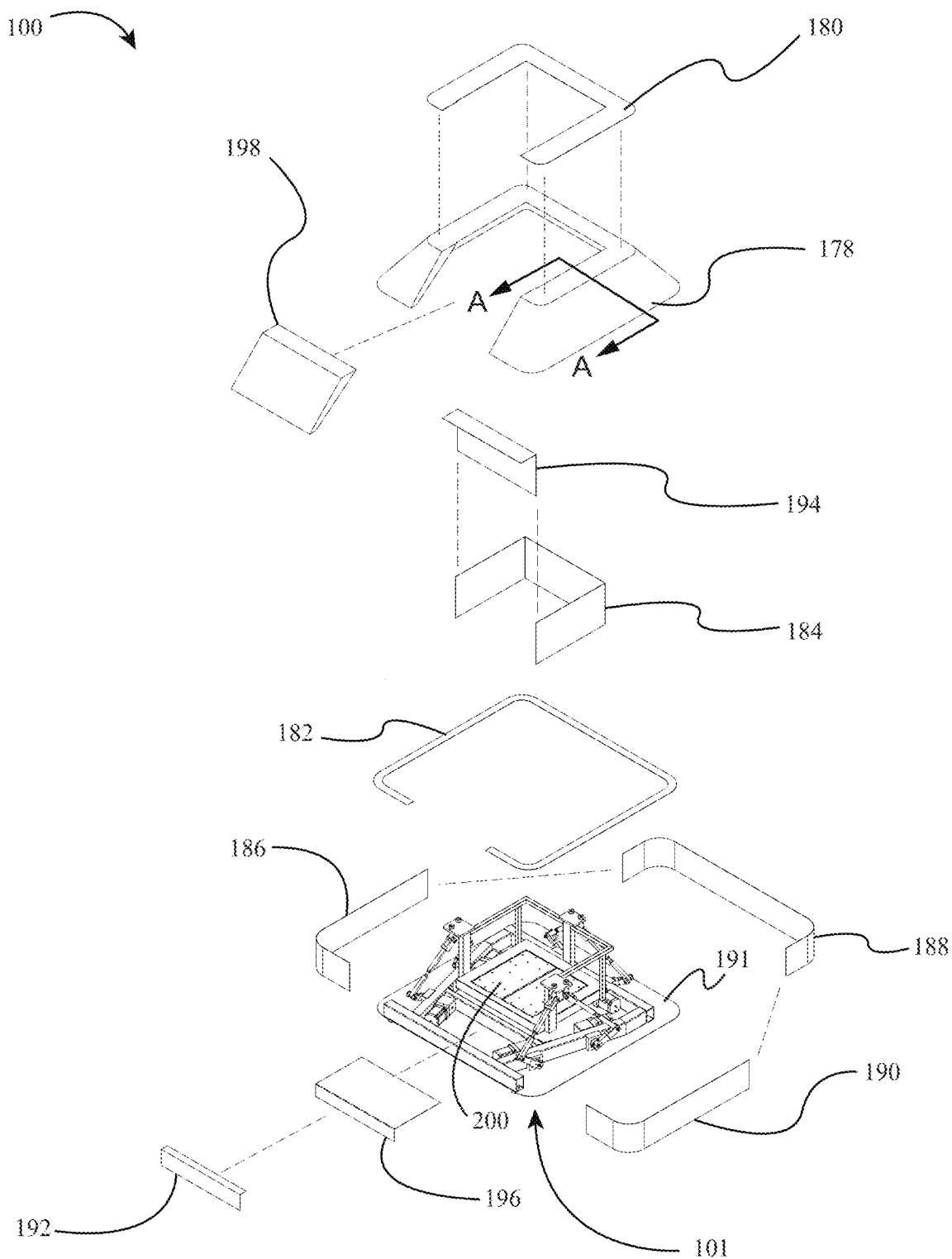
FIG. 7 is a partially exploded perspective view of the motion base of FIG. 1, wherein the cover members have been removed from the internal assembly of the motion base.

In the illustrative embodiment, with combined reference to FIGS. 1, 6, and 7, it can be seen that the rear of the motion base 100 is provided with a removable cover assembly 194, 198 so as to allow a person to easily gain access to the force plate 200 in the middle of the motion base 100. In the illustrative embodiment, the removable cover assembly 194, 198 comprises an L-shaped front cover member 194 and a diagonal rear cover member 198. In the illustrative embodiment, the removable cover assembly 194, 198 can be completely removed from the remainder of the motion base 100. Alternatively, the cover assembly 194, 198 could be hinged (i.e., like a door) so that it could be opened when a person needs to gain access to the force plate 200 in the middle of the motion base 100.

Next, referring again to FIG. 16, the immersive visual display device 212 of the force measurement system 210 will be described in further detail. In the illustrative embodiment, as shown in FIG. 16, the immersive visual display device 212 generally comprises a generally hemispherical concave projection screen 214 with a peripheral flange 216 therearound, and a projector 220 having a fisheye lens 224 mounted on the top of the hemispherical projection screen 214. In FIG. 16, it can be seen that the fisheye lens 224 is connected to the body of the projector 220 by an elbow fitting 222. As illustrated in FIG. 16, the fisheye lens 224 is disposed at approximately the apex of the hemispherical projection screen 214, and it extends down through the cutout 228 at the top of the screen 214. In order to permit a subject 236 to be substantially circumscribed by the generally hemispherical projection screen 214 on three sides, the bottom of the screen 214 is provided with a semi-circular cutout 218 in the illustrative embodiment.

Referring again to FIG. 16, it can be seen that the generally hemispherical projection screen 214 can be supported from a floor surface using a screen support structure that is used to elevate the projection screen 214 a predetermined distance above the floor of a room. With continued reference to FIG. 16, it can be seen that the illustrated screen support structure comprises a plurality of lower leg members 232 (i.e., four (4) leg members 232) that support an upper support cage portion 230, which is disposed around the upper portion of the generally hemispherical projection screen 214. In particular, the upper support cage portion 230 is securely attached to the peripheral flange 216 of the hemispherical projection screen 214 (e.g., by using a plurality of fasteners on each side of the flange 216). Because the upper support cage portion 230 is mostly attached to the upper portion (e.g., upper half) of the screen 214, the screen 214 is generally supported above its center-of-gravity, which advantageously results in a screen mounting arrangement with high structural stability. As shown in FIG. 16, one pair of the plurality of lower leg members 232 are disposed on each of the opposed lateral sides of the screen 214. Also, it can be seen that each of the lower leg members 232 is provided with a height-adjustable foot 234 for adjusting the height of the screen 214 relative to the floor. Also, as shown in FIG. 16, the projector 220 is supported on the top of the screen 214 by a projector support frame 226, which is secured directly to the upper support cage portion 230 of the screen support structure so as to minimize the transmission of vibrations from the projector 220 to the hemispherical projection screen 214.

It is readily apparent from the above detailed description that the aforedescribed motion base 100 offers numerous advantages. For example, the advantages of the motion base 100 and associated force measurement system of the illustrative embodiment include: (i) six (6) degree-of-freedom (DOF) motion, which allows translations and rotations in every direction; (ii) the maximum range of motion is increased in all directions/rotations as compared to conventional motion bases; (iii) the force plate 200 is able to measure all forces and moments; (iv) modular custom powertrain and electronics allow for lower cost to produce the motion base 100; (v) the motion base 100 has a smaller footprint as compared to conventional motion bases; and (vi) the motion base 100 is provided with user-friendly motion controls that allow for complex movements.

Now, the features of a second illustrative motion base for displacing an object above a support surface will be described in detail. In the second illustrative embodiment, the motion base generally comprises a base assembly; a support structure configured to be coupled to an object, the support structure being rotatably coupled to the base assembly about a transverse rotational axis, the transverse rotational axis being disposed beneath a top surface of the object; and an actuation system, the actuation system including one or more actuators operatively coupled to the support structure, and the one or more actuators configured to rotate the support structure relative to the base assembly about the transverse rotational axis and translate the support structure so as to simulate a rotation of the support structure about an imaginary rotational axis disposed above the top surface of the object.

In the second illustrative embodiment, the one or more actuators of the motion base comprise a first actuator configured to rotate the support structure about the transverse rotational axis and a second actuator configured to translate the support structure.

In the second illustrative embodiment, the one or more actuators are configured to simultaneously translate the support structure while rotating the support structure about the transverse rotational axis so as to simulate the rotation of the support structure about the imaginary rotational axis disposed above the top surface of the object.

Figure 11:
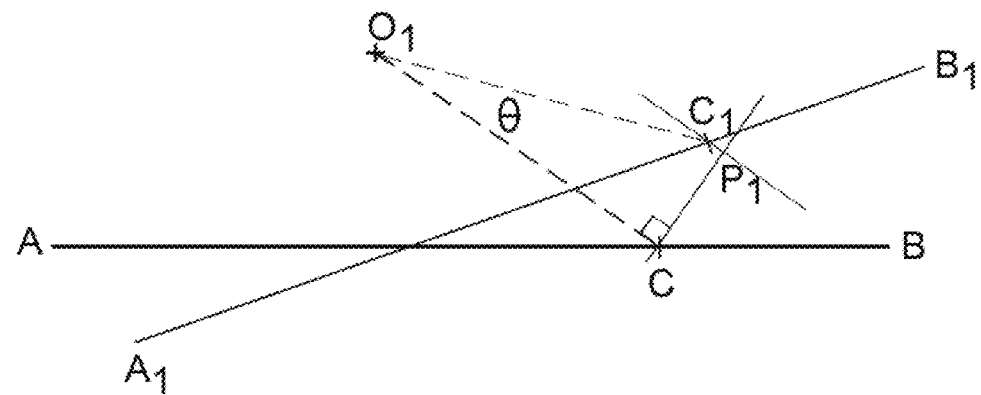
FIG. 11 is a first diagram illustrating rotation of an exemplary line disposed on an object supported on a motion base when the axis of rotation is disposed above the top surface of the object, according to an illustrative embodiment.

For example, with reference to the diagram in FIG. 11, suppose the line AB disposed on an object supported on a motion base is rotated counter-clockwise about a point $O_1$ by an angle $\theta$, such that the point A moves to $A_1$, B moves to $B_1$, and any given point on the line C moves to $C_1$. If the line $CP_1$ is perpendicular to $O_1C$, then the location of $C_1$ can be given as the vector sum of $CP_1$ and $P_1C_1$. Using geometric relationships, the distance $CP_1$ is calculated as $O_1C$ times the sine of angle $\theta$ (note that distance $O_1C$ is equal to $O_1C_1$). Similarly, the distance $P_1C_1$ is equal to $O_1C$ times (1−cosine $\theta$). If $\theta$ is small (say less than 10 degrees), then cosine $\theta$ is close to one, and therefore the distance $P_1C_1$ is close to zero.

Figure 12:
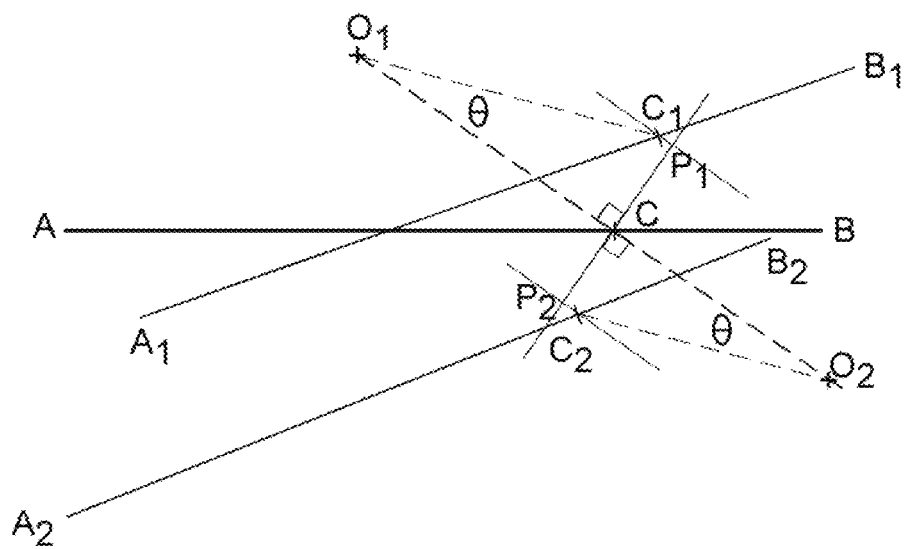
FIG. 12 is a second diagram illustrating rotation of the exemplary line on the object supported on the motion base when the axis of rotation is disposed below the top surface of the object.

Now, referring to FIG. 12, if the line AB is rotated in the same direction, and by the same amount about another point located along the line $O_1C$, for example about $O_2$ as seen in FIG. 12, then line AB becomes $A_2B_2$, and point C moves to $C_2$. Similarly, $P_2C$ is given as $O_2C$ times sine of angle $\theta$, and $P_2C_2$ would be negligible small when $\theta$ is small.

Next, if line $A_2B_2$ is moved along a line perpendicular to $O_1O_2$, by the distance $P_2P_1$, then, excluding the small error in the direction joining the two center of rotations, line $A_2B_2$ will coincide with $A_1B_1$. As such, it follows that if the linear motion is executed simultaneously with the rotation, then rotation about $O_1$ as compared to simultaneously rotating about $O_2$ and translating by the distance $O_1 O_2$ times the sine of angle θ will result in identical motion for line AB.

Figure 13:
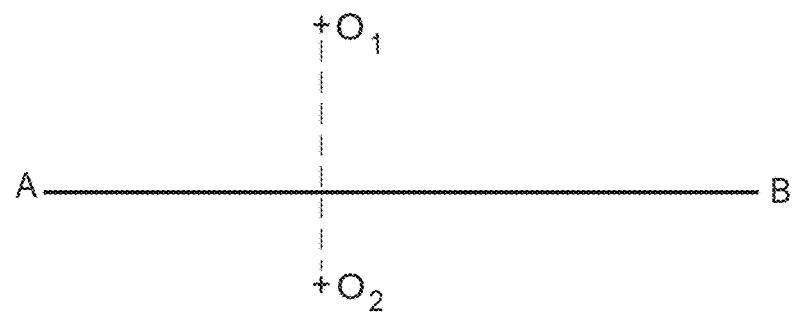
FIG. 13 is a third diagram illustrating translation of the exemplary line on the object supported on the motion base to a displaced position that approximates the same displaced position as that depicted in FIG. 11.

If $O_2$ is chosen along a line passing through $O_1$ which is perpendicular to AB, as shown in FIG. 13, then rotating about $O_2$ and simultaneously making a translational correction equal to the distance $O_1 O_2$ times the sine of the angular rotation along line AB would result in the same motion as rotating about $O_1$. Therefore, the motion base center of rotation is able to be moved to a point under the top surface of the object (e.g., a force plate) being support thereon, and it is possible to duplicate a rotation about a point above the top surface of the object (e.g., the force plate).

In the second illustrative embodiment, as described above for the first illustrative embodiment, the motion base may be provided as part of a force measurement system 310, where the motion base is used for displacing the force measurement assembly (e.g., the force plate or balance plate) of the force measurement system. In FIG. 15, constituent components of the illustrative force measurement system 210, 310 comprising the motion base are diagrammatically depicted. FIG. 15 is applicable to both force measurement systems 210, 310 described herein. In the illustrative embodiment, the force measurement assembly of the force measurement system is configured to receive a subject thereon. Also, in the illustrative embodiment, the force measurement assembly is coupled to the support structure of the motion base, and the transverse rotational axis of the motion base is disposed beneath a top surface of the force measurement assembly. The actuation system of the motion base is configured to simultaneously translate the force measurement assembly while rotating the force measurement assembly about the transverse rotational axis so as to simulate the rotation of the force measurement assembly about an imaginary rotational axis disposed above the top surface of the force measurement assembly.

In the first and second illustrative embodiments described above, the force measurement assembly (e.g., force plate 200) includes a plurality of force transducers (e.g., force transducer beams or pylon-type load cells) so that the loads being applied to the top surface of the force measurement assembly can be measured. In the illustrative embodiment, each of the force transducers may comprise a plurality of strain gages for detecting the deformation in the force transducer frame resulting from the applied load. For example, in the illustrative embodiment, the force transducers of the force measurement assembly may be sensitive to the vertical force ($F_z$) and the moments in the x and y directions ($M_x$, $M_y$). Alternatively, the force transducers of force measurement assembly may be sensitive to all six (6) force and moment components ($F_x$, $F_y$, $F_z$, $M_x$, $M_y$, $M_z$).

In the illustrative embodiment, each of the force transducers of the force measurement assembly includes a plurality of strain gages wired in one or more Wheatstone bridge configurations, wherein the electrical resistance of each strain gage is altered when the associated portion of the force transducer undergoes deformation resulting from the load (i.e., forces and/or moments) acting on a top plate component of the force measurement assembly. For each plurality of strain gages disposed on the force transducers, the change in the electrical resistance of the strain gages brings about a consequential change in the output voltage of the Wheatstone bridge (i.e., a quantity representative of the load being applied to the measurement surface). In the illustrative embodiment, each force transducer outputs a plurality of analog output voltages (signals).

In the illustrative embodiment, referring to FIG. 15, the data acquisition and processing device 14 (i.e., computing device 14) of the force measurement system 210, 310 may comprise a microprocessor 16 for processing data from the force transducers or load cells 22 of the force measurement assembly, memory 18 (e.g., random access memory or RAM) for storing data during the processing thereof, and data storage device(s) 20, such as one or more hard drives, compact disk drives, floppy disk drives, flash drives, or any combination thereof. Also, the data acquisition and processing device 14 may comprise user input devices in the form of a keyboard, mouse, and touchpad or touchscreen.

In the illustrative embodiment, the force measurement assembly may comprise a dedicated digitizer and signal conditioner that is electrically coupled to each of the force transducers or load cells 22 of the force measurement assembly by electrical transducer wiring. The digitizer and signal conditioner converts the analog voltage signals from the force transducers or load cells 22 of the force measurement assembly into digital voltage signals, and may also perform other functions on the signals as well, such as amplification, filtering, etc. In the illustrative embodiment, the force plate digitizer and signal conditioner is electrically coupled to the data acquisition and processing device 14 by an electrical cable so that the signals from the force transducers or load cells 22 of the force measurement assembly may be converted into output loads (i.e., into forces and/or moments) by multiplying the voltage signals by a calibration matrix. Alternatively, the force plate digitizer and signal conditioner may convert the signals from the force transducers or load cells 22 of the force measurement assembly into output loads (i.e., into forces and/or moments) by multiplying the voltage signals by a calibration matrix.

In the illustrative embodiment, the data acquisition and processing device 14 is also operatively coupled to the actuators 10 of the motion base in a bidirectional data flow manner so as to allow data to be transferred in both directions between the motion base and the data acquisition and processing device 14. For example, motion base control signals are sent from the data acquisition and processing device 14 to the actuators 10 of the motion base, and feedback data in the form of motion base position, velocity, and acceleration is sent from the motion base to the data acquisition and processing device 14. The motion base control signals control the rotation and translation of the motion base.

In the illustrative embodiment, when the motion base is provided as part of the force measurement system 210, 310, the motion base may displace the force measurement assembly disposed thereon in accordance with a scene being displayed on the system visual display device. For example, if an inclined ground surface is being displayed in the scene on the system visual display device, then the force measurement assembly may be tilted by the motion base so that it assumes an inclined position corresponding to the inclined ground surface in the scene.

In the first and second illustrative embodiments described above, the force measurement assembly of the force measurement system 210, 310 is used for collecting force and/or moment data used in computerized dynamic posturography (CDP) testing and/or training performed on a patient. For example, the force measurement assembly may comprise the CDP force measurement assembly 102 described in U.S. Pat. No. 11,540,744, the entire disclosure of which is incorporated herein by reference. In such a CDP force measurement system, by using the motion base described in the second illustrative embodiment, it is possible to duplicate a rotation about the ankle joint of a subject by simultaneously making a linear motion correction along the antero-posterior direction of the plate. That is, instead of rotating the CDP's force measurement assembly (e.g., balance plate) at the ankle level, by using the motion base described herein, the force measurement assembly is able to be rotated below the top surface of the force measurement assembly, but translated simultaneously in the fore-aft direction so that the force measurement assembly actually moves as if the assembly is rotated at the ankle level. In the displacement of the force measurement assembly, there is a negligible vertical error which can be easily neglected. Advantageously, utilizing the motion base described herein obviates the need for the sides of the base assembly to extend above the ankles of the subject, thereby allowing the CDP base assembly to be made far more compact.

Figure 14:
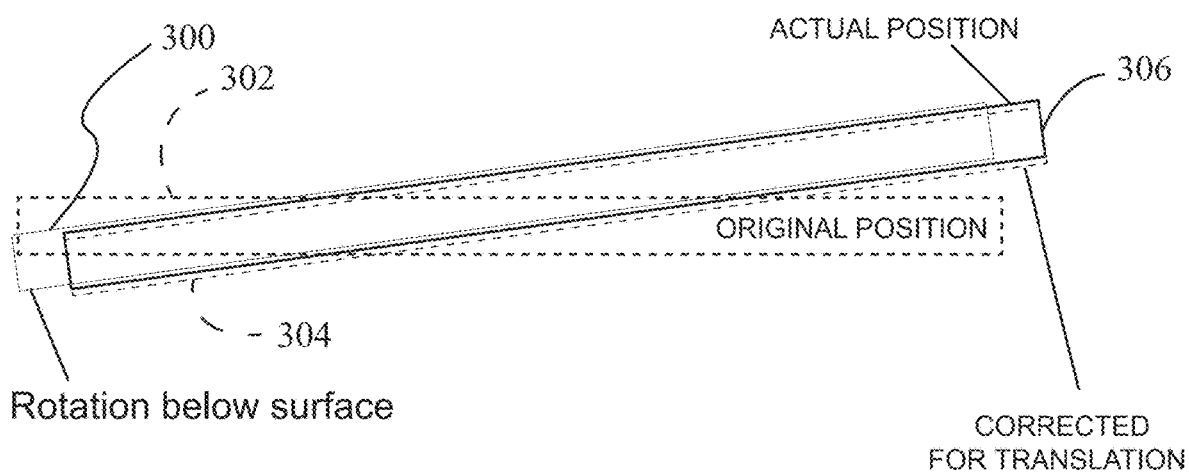
FIG. 14 is a fourth diagram illustrating simultaneous translation and rotation of a force plate about an axis of rotation below the top surface of the force plate that approximates rotation of the force plate about an axis of rotation above the top surface, according to a second illustrative embodiment.

As one example, in the CDP force measurement system, if the force measurement assembly is rotated 25 mm below the top surface of the force measurement assembly instead of 125 mm above the top surface, at a maximum rotation of 8-degrees, a vertical error of 1.5 mm and a horizontal error of 20.9 mm results. One can compensate for the horizontal error by moving the plate horizontally in proportion and in synchrony with the rotation. The small vertical error can be ignored, thus resulting in virtually the same motion produced by simultaneously translating the force measurement assembly and rotating the force measurement assembly about a rotational axis 25 mm below its top surface that is produced by rotating the force measurement assembly about a rotational axis 125 mm above its top surface. FIG. 14 diagrammatically depicts, for 8-degree rotation as one example, simultaneous translation and rotation of a force plate about an axis of rotation below the top surface of the force plate that approximates rotation of the force plate about an axis of rotation above the top surface. In FIG. 14, the original position of the force plate is denoted by dashed outline 302, while the actual position of the force plate is denoted by solid outline 306. The rotation of the force plate below surface is denoted by solid outline 300, while the dashed outline 304 denotes the outline of the force plate corrected for translation.

While a force measurement assembly (e.g., a force plate or balance plate) is attached to the support structure of the motion base in the second illustrative embodiment, it is to be understood that, in alternative embodiments of the invention, other objects may be attached to the support structure of the motion base in lieu of the force measurement assembly. For example, other force measurement assemblies, such as instrumented treadmills, may be attached to the support structure of the motion base. Also, objects other force measurement assemblies, such as flight simulators and virtual reality simulators, may also be attached to the support structure of the motion base. As such, the motion base may be used for displacing a myriad of different objects attached to the motion base support structure thereof.

It is readily apparent from the above detailed description that the aforedescribed motion base offers numerous advantages. For example, the motion base described herein has a rotational axis disposed beneath a top surface of an object being rotated so as to simplify the structural configuration of the motion base.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A motion base for displacing an object above a support surface, the motion base comprising:
   a base support structure having a motor coupled thereto;
   a displaceable carriage configured to be coupled to the object, the displaceable carriage having a support surface configured to support both a first foot and a second foot of a person within the displaceable carriage; and
   an actuation system, the actuation system including one or more actuators operatively coupling the displaceable carriage to the base support structure, the one or more actuators configured to displace the displaceable carriage, the first foot of the person, and the second foot of the person relative to the base support structure, and at least one of the one or more actuators including a rotation member rotated by the motor at a bottom end thereof;
   wherein a top end of the at least one of the one or more actuators is mounted to the displaceable carriage such that the support surface of the displaceable carriage is suspended below the top end of the at least one of the one or more actuators of the actuation system.

2. The motion base according to claim 1, wherein the base support structure at least partially surrounds the displaceable carriage.

3. The motion base according to claim 1, wherein the displaceable carriage comprises a top frame section, a bottom frame section, and at least one vertical frame member connected between the bottom frame section and the top frame section.

4. The motion base according to claim 3, wherein the base support structure comprises at least one frame member disposed beneath a bottom surface of the displaceable carriage, and the at least one of the one or more actuators of the actuation system is coupled between the at least one frame member of the base support structure and the top frame section of the displaceable carriage, and the at least one of the one or more actuators includes a plurality of rotation members rotated by the motor.

5. The motion base according to claim 3, wherein the displaceable carriage has a basket shape with one open side, the object is coupled to the displaceable carriage, and the object comprises a force measurement assembly that collects force and/or moment data used in computerized dynamic posturography (CDP) testing and/or training performed on the person, the force and/or moment data collected by the force measurement assembly including vertical force data.

6. The motion base according to claim 3, wherein the one or more actuators of the actuation system comprise a plurality of actuators, each of the plurality of actuators being coupled between a respective frame member of the base support structure and the top frame section of the displaceable carriage.

7. The motion base according to claim 6, wherein a rotatable upper end of at least one of the plurality of actuators is coupled to the top frame section of the displaceable carriage by a mounting plate.

8. The motion base according to claim 1, wherein the motion base has at least two degrees of freedom.

9. The motion base according to claim 8, wherein the motion base has six degrees of freedom.

10. The motion base according to claim 1, wherein the object is coupled to the displaceable carriage, and the object comprises a force measurement assembly, and the force measurement assembly comprises:
   a top surface for receiving at least one portion of a body of the person; and
   at least one force transducer, the at least one force transducer configured to sense one or more measured quantities and output one or more signals that are representative of forces and/or moments being applied to the top surface of the force measurement assembly by the person.

11. The motion base according to claim 10, further comprising one or more data processing devices operatively coupled to the actuation system of the motion base and the force measurement assembly, the one or more data processing devices configured to receive the one or more signals that are representative of the forces and/or moments being applied to the top surface of the force measurement assembly by the person, and to convert the one or more signals into output forces and/or moments, the one or more data processing devices further configured to selectively displace the force measurement assembly using the actuation system of the motion base.

12. A motion base for displacing an object above a support surface, the motion base comprising:
   a base assembly having a motor coupled thereto;
   a support structure configured to be coupled to the object, the support structure comprising a displaceable carriage configured to be coupled to the object, the displaceable carriage having a support surface configured to support both a first foot and a second foot of a person within the displaceable carriage and being rotatably coupled to the base assembly about a transverse rotational axis, the transverse rotational axis being disposed beneath a top surface of the object;
   an actuation system, the actuation system including one or more actuators operatively coupled to the support structure, at least one of the one or more actuators including a rotation member rotated by the motor at a bottom end thereof,
   wherein a top end of the at least one of the one or more actuators is mounted to the displaceable carriage such that the support surface of the displaceable carriage is suspended below the top end of the at least one of the one or more actuators of the actuation systems, and the one or more actuators configured to rotate the support structure relative to the base assembly about the transverse rotational axis and translate the support structure so as to simulate a rotation of the support structure about an imaginary rotational axis disposed above the top surface of the object; and
   one or more data processing devices operatively coupled to the actuation system, the one or more data processing devices configured to generate control signals that rotate the support structure relative to the base assembly about the transverse rotational axis and translate the support structure, thereby simulating the rotation of the support structure about the imaginary rotational axis disposed above the top surface of the object.

13. The motion base according to claim 12, wherein the support structure is coupled to the object, and the one or more actuators are configured to simultaneously translate the support structure while rotating the support structure about the transverse rotational axis so as to simulate the rotation of the support structure about the imaginary rotational axis disposed above the top surface of the object.

14. The motion base according to claim 12, wherein the object is coupled to the support structure, and the object comprises one of: (i) an instrumented treadmill, (ii) a force plate, (iii) a flight simulator, and (iv) a virtual reality simulator.

15. The motion base according to claim 12, wherein the one or more actuators comprise a first actuator configured to rotate the support structure about the transverse rotational axis and a second actuator configured to translate the support structure.

16. A motion base for displacing a force measurement assembly, the motion base comprising:
   a base assembly having a motor coupled thereto;
   a support structure configured to be coupled to the force measurement assembly, the support structure comprising a displaceable carriage configured to be coupled to the force measurement assembly, the displaceable carriage having a support surface configured to support both a first foot and a second foot of a person within the displaceable carriage and being rotatably coupled to the base assembly about a transverse rotational axis, the transverse rotational axis being disposed beneath a top surface of the force measurement assembly;
   an actuation system, the actuation system including one or more actuators operatively coupled to the support structure, at least one of the one or more actuators including a rotation member rotated by the motor at a bottom end thereof,
   wherein a top end of the at least one of the one or more actuators is mounted to the displaceable carriage such that the support surface of the displaceable carriage is suspended below the top end of the at least one of the one or more actuators of the actuation systems, and the one or more actuators configured to rotate the support structure relative to the base assembly about the transverse rotational axis and translate the support structure so as to simulate a rotation of the support structure about an imaginary rotational axis disposed above the top surface of the force measurement assembly; and
   one or more data processing devices operatively coupled to the actuation system of the motion base and the force measurement assembly, the one or more data processing devices configured to generate control signals that rotate the support structure relative to the base assembly about the transverse rotational axis and translate the support structure, thereby simulating the rotation of the support structure about the imaginary rotational axis disposed above the top surface of the force measurement assembly.

17. The motion base according to claim 16, wherein the one or more actuators are configured to simultaneously translate the support structure while rotating the support structure about the transverse rotational axis so as to simulate the rotation of the support structure about the imaginary rotational axis disposed above the top surface of the force measurement assembly.

18. The motion base according to claim 16, wherein the force measurement assembly comprises one of: (i) an instrumented treadmill and (ii) a force plate.

19. The motion base according to claim 16, wherein the force measurement assembly is configured to acquire force and/or moment data used in computerized dynamic posturography (CDP) testing and/or training performed on a person.

20. The motion base according to claim 16, wherein the one or more actuators comprise a first actuator configured to rotate the support structure about the transverse rotational axis and a second actuator configured to translate the support structure.

* * * * *